(12) United States Patent
Nojima et al.

(10) Patent No.: US 7,910,557 B2
(45) Date of Patent: Mar. 22, 2011

(54) HAIR CARE PRODUCT

(75) Inventors: Jun Nojima, Shinichi-cho (JP); Yasuo Miyake, Shinichi-cho (JP); Nobuaki Ohto, Shinichi-cho (JP)

(73) Assignee: Maruzen Pharmaceuticals Co., Ltd., Onomichi-shi, Hiroshima (JP)

(*) Notice: Subject to any disclaimer, the term of this patent is extended or adjusted under 35 U.S.C. 154(b) by 0 days.

(21) Appl. No.: 12/585,674

(22) Filed: Sep. 22, 2009

(65) Prior Publication Data

US 2010/0048703 A1  Feb. 25, 2010

Related U.S. Application Data

(62) Division of application No. 11/884,750, filed as application No. PCT/JP2006/302560 on Feb. 14, 2006, now abandoned.

(30) Foreign Application Priority Data

Feb. 22, 2005 (JP) .................................. 2005-046151

(51) Int. Cl.
    *A01N 45/00* (2006.01)
(52) U.S. Cl. .......................................... 514/26
(58) Field of Classification Search ...................... 514/26
    See application file for complete search history.

(56) References Cited

U.S. PATENT DOCUMENTS

| 6,485,760 B2 | 11/2002 | Matsuyama |
| 2005/0020681 A1 | 1/2005 | Takayama et al. |

FOREIGN PATENT DOCUMENTS

| EP | 1 022 022 A | 7/2000 |
| JP | 07-138135 A | 5/1995 |
| JP | A-09-208431 | 8/1997 |
| JP | A-11-012134 | 1/1999 |
| JP | A-2000-169384 | 6/2000 |
| JP | 2001-187742 A | 7/2001 |
| JP | 2002-068942 A | 3/2002 |
| JP | A-2002-087976 | 3/2002 |
| JP | A-2002-241296 | 8/2002 |
| JP | A-2002-241297 | 8/2002 |
| JP | A-2003-055162 | 2/2003 |
| JP | A-2003-160503 | 6/2003 |
| JP | A-2003-192541 | 7/2003 |
| JP | A-2004-215562 | 8/2004 |
| JP | A-2005-002068 | 1/2005 |
| JP | A-2005-29570 | 2/2005 |
| WO | WO 02/43681 A1 | 6/2002 |
| WO | WO 2004/052381 | 6/2004 |

OTHER PUBLICATIONS

"International Cosmetic Ingredient Dictionary and Handbook," 9th Edition (2002), *The Cosmetic Toiletry, and Fragrance Association*, XP-002540625, p. 596.
Z. Z. Liang, et al., "Polyhydroxylated Triterpenes from *Eriobotrya japonica*," Planta Medica, vol. 56, No. 3 (1990), pp. 330 to 332.
M. Hardy, "The secret life of the hair follicle," Trends Genet, *Elsevier Science Publishers, Ltd.*, vol. 8 (1992), pp. 55-61(discussed on p. 6 of the specification).
"Antiaging Series No. 1 Hair graying, loss and growth in practice," *NTS Inc.* (2005), pp. 91-104 (discussed on pp. 4 and 6 of the specification) (concise English explanation of relevance enclosed).
A. H. Reddi, "Bone Morphogenetic Proteins: an Unconventional Approach to Isolation of First Mammalian Morphogens," *Cytokine & Growth Factor Reviews*, vol. 8, No. 1 (1997), pp. 11-20 (discussed on p. 6 of the specification).
Extended European Search Report mailed on Aug. 28, 2009 issued from the European Patent Office in the corresponding European patent application No. 06713701.8 -2108.

*Primary Examiner* — Raymond J Henley, III
(74) *Attorney, Agent, or Firm* — Posz Law Group, PLC

(57) ABSTRACT

A substance having a testosterone 5α-reductase inhibiting action, a hair papilla cell growth promoting action, a fibroblast growth factor-7 production promoting action, a vascular endothelial growth factor production promoting action or a bone morphogenetic protein-2 production promoting action, and a hair care product having this substance blended therein. A hair growth tonic, a testosterone 5α-reductase inhibitor, a hair papilla cell growth promoter, a fibroblast growth factor-7 production promoter, a vascular endothelial growth factor production promoter and a bone morphogenetic protein-2 production promoter each having this substance, such as corosolic acid, as an active ingredient thereof.

7 Claims, No Drawings

SEQUENCE LISTING

<160> NUMBER OF SEQ ID NOS: 12

<210> SEQ ID NO 1
<211> LENGTH: 511
<212> TYPE: RNA

<213> ORGANISM: Homo sapiens

<400> SEQUENCE: 1

| | | | | | |
|---|---|---|---|---|---|
| acgagauguc | uaguacgaaa | guguaauaga | cagaucaccc | augauauaga | aaucgaacgu | 60 |
| uacuguacug | aggucucguu | uaccgauguu | uacacuugac | aaggucggga | cucgcugugu | 120 |
| guucuucaau | acuaauguac | cuuccucccc | uauauucuca | cucuucugag | aagacagcuu | 180 |
| gugucaccau | ggacuccuag | cuauuuucuc | cguucauuu | ucccuggguu | ucuacuucu | 240 |
| uauuaauguu | auaguaccuu | uagccuguc | accgucaacc | uuaacaccgu | uaguucccc | 300 |
| accuuucacu | uaagauagaa | cguuacugu | uccuuccuuu | ugagauacgu | uucuuucuua | 360 |
| cguuacuucu | aacauuguug | uuucuugauu | aagaccuuuu | gguaauguug | uguauacgua | 420 |
| gucgauuuac | cuguguguug | ccuccccuuu | acaaacaacg | gaauuuaguu | ucccccuaag | 480 |
| gacauucucc | uuuuuuuugc | uucuuucuug | u | | | 511 |

<210> SEQ ID NO 2
<211> LENGTH: 496
<212> TYPE: RNA
<213> ORGANISM: Homo sapiens

<400> SEQUENCE: 2

| | | | | | |
|---|---|---|---|---|---|
| ccaggguccg | acgugggaug | cgucuuccuc | cucccgucuu | aguagugcuu | caccacuuca | 60 |
| aguaccuaca | gauagucgcg | ucgaugacgg | uagguuagcu | cugggaccac | cuguagaagg | 120 |
| uccucauggg | acuacucuag | cucauguaga | aguucgguag | gacacacggg | gacuacgcua | 180 |
| cgcccccgac | gacguuacug | cucccggacc | ucacacacgg | gugacuccuc | agguuguagu | 240 |
| gguacgucua | auacgccuag | uuuggagugg | uuccggucgu | guauccucuc | uacucgaagg | 300 |
| augucguguu | guuuacacuu | acgucuggu | ucuuucuauc | ucguucuguu | cuuuuuuua | 360 |
| gucaagcucc | uuucccuuuc | cccguuuuug | cuuucgcguu | cuuuagggcc | auauucagga | 420 |
| ccucgcaagg | gacacccgga | acgagucucg | ccucuuucgu | aaacaaacau | guucaggcg | 480 |
| ucugcacauu | uacaag | | | | | 496 |

<210> SEQ ID NO 3
<211> LENGTH: 625
<212> TYPE: RNA
<213> ORGANISM: Homo sapiens

<400> SEQUENCE: 3

| | | | | | |
|---|---|---|---|---|---|
| uuuaaggggc | acuggucuga | aaaccugugg | uccaaccacu | uagucuuacg | uucguccacc | 60 |
| cuuucaaaac | uacaguggg | gcgacacuac | gccaccugac | gugucccugu | gcgguuggua | 120 |
| ccuaagcacc | accuucaccg | ggugaaccuc | cucuuuguuc | cacagagguu | ucuguacaa | 180 |
| uccuauucgu | ccagaaacgu | gguucuacuu | gugucgacca | gugucuauuc | cgguaacgau | 240 |
| cauugaaaac | cgguacuacc | uuuucccgua | ggagaggugu | uuucucuuuu | ugcaguucgg | 300 |
| uuuguguuug | ucgccuuugc | ggaauucagg | ucgacauucu | cuguggaaa | caugcaccug | 360 |
| aagucacugc | accccaccuu | acugaccuaa | caccgagggg | gccccauagu | gcggaaaaug | 420 |
| acggugccuc | uuacgggaaa | aggagaccga | cuaguagacu | ugaggugauu | aguacgguaa | 480 |
| caagucugca | accaguugag | acaauugaga | uucuaaggau | uccguacgac | acagggcugu | 540 |
| cuugagucac | gauagagcua | cgacauggaa | cugcucuuac | uuuuccaaca | uaauuucuug | 600 |
| auaguccugu | accaacaccu | cccaa | | | | 625 |

<210> SEQ ID NO 4

```
<211> LENGTH: 511
<212> TYPE: DNA
<213> ORGANISM: Homo sapiens

<400> SEQUENCE: 4
tgctctacag atcatgcttt cacattatct gtctagtggg tactatatct ttagcttgca     60
atgacatgac tccagagcaa atggctacaa atgtgaactg ttccagccct gagcgacaca    120
caagaagtta tgattacatg aaggaggggg atataagagt gagaagactc ttctgtcgaa    180
cacagtggta cctgaggatc gataaaagag gcaaagtaaa agggacccaa gagatgaaga    240
ataattacaa tatcatggaa atcaggacag tggcagttgg aattgtggca atcaaagggg    300
tggaaagtga attctatctt gcaatgaaca aggaaggaaa actctatgca agaaagaat     360 gcaatgaaga ttgtaacttc aaagaactaa ttctggaaaa ccattacaac acatatgcat    420
cagctaaatg gacacacaac ggaggggaaa tgtttgttgc cttaaatcaa aaggggattc    480
ctgtaagagg aaaaaaaacg aagaaagaac a                                   511

<210> SEQ ID NO 5
<211> LENGTH: 496
<212> TYPE: DNA
<213> ORGANISM: Homo sapiens

<400> SEQUENCE: 5
ggtcccaggc tgcacccatg gcagaaggag gagggcagaa tcatcacgaa gtggtgaagt     60
tcatggatgt ctatcagcgc agctactgcc atccaatcga ccctggtg acatcttcc       120 aggagtaccc tgatgagatc gagtacatct tcaagccatc ctgtgtgccc ctgatgcgat    180 gcggggctg ctgcaatgac gagggcctgg agtgtgtgcc cactgaggag tccaacatca    240
ccatgcagat tatgcggatc aaacctcacc aaggccagca cataggagag atgagcttcc    300
tacagcacaa caaatgtgaa tgcagaccaa agaaagatag agcaagacaa gaaaaaaaat    360
cagttcgagg aaagggaaag gggcaaaaac gaaagcgcaa gaaatcccgg tataagtcct    420
ggagcgttcc ctgtgggcct tgctcagagc ggagaaagca tttgtttgta caagatccgc    480
agacgtgtaa atgttc                                                   496

<210> SEQ ID NO 6
<211> LENGTH: 625
<212> TYPE: DNA
<213> ORGANISM: Homo sapiens

<400> SEQUENCE: 6
aaattccccg tgaccagact tttggacacc aggttggtga atcagaatgc aagcaggtgg     60
gaaagttttg atgtcacccc cgctgtgatg cggtggactg cacagggaca cgccaaccat    120
ggattcgtgg tggaagtggc ccacttggag gagaaacaag gtgtctccaa gagacatgtt    180
aggataagca ggtctttgca ccaagatgaa cacagctggt cacagataag gccattgcta    240 gtaactttg gccatgatgg aaaagggcat cctctccaca aaagagaaaa acgtcaagcc    300
aaacacaaac agcggaaacg ccttaagtcc agctgtaaga gacacccttt gtacgtggac    360
ttcagtgacg tggggtggaa tgactggatt gtggctcccc cggggtatca cgccttttac    420
tgccacggag aatgcccttt tcctctggct gatcatctga actccactaa tcatgccatt    480
gttcagacgt tggtcaactc tgttaactct aagattccta aggcatgctg tgtcccgaca    540
gaactcagtg ctatctcgat gctgtaccct gacgagaatg aaaaggttgt attaagaac     600 tatcaggaca tggttgtgga gggtt                                         625
```

```
<210> SEQ ID NO 7
<211> LENGTH: 20
<212> TYPE: DNA
<213> ORGANISM: Artificial Sequence
<220> FEATURE:
<223> OTHER INFORMATION: Sequence of PCR primer

<400> SEQUENCE: 7
gacatggatc ctgccaactt                                                20

<210> SEQ ID NO 8
<211> LENGTH: 20
<212> TYPE: DNA
<213> ORGANISM: Artificial Sequence
<220> FEATURE:
<223> OTHER INFORMATION: Sequence of PCR primer

<400> SEQUENCE: 8
ctacctccac catgccaagt                                                20

<210> SEQ ID NO 9
<211> LENGTH: 21
<212> TYPE: DNA
<213> ORGANISM: Artificial Sequence
<220> FEATURE:
<223> OTHER INFORMATION: Sequence of PCR primer

<400> SEQUENCE: 9
tcataaaacc tgcaacagcc a                                              21

<210> SEQ ID NO 10
<211> LENGTH: 21
<212> TYPE: DNA
<213> ORGANISM: Artificial Sequence
<220> FEATURE:
<223> OTHER INFORMATION: Sequence of PCR primer

<400> SEQUENCE: 10
ggaagaaagt gggctgtttt t                                              21

<210> SEQ ID NO 11
<211> LENGTH: 20
<212> TYPE: DNA
<213> ORGANISM: Artificial Sequence
<220> FEATURE:
<223> OTHER INFORMATION: Sequence of PCR primer

<400> SEQUENCE: 11
gcgagtctgt gttttgcag                                                 20

<210> SEQ ID NO 12
<211> LENGTH: 20
<212> TYPE: DNA
<213> ORGANISM: Artificial Sequence
<220> FEATURE:
<223> OTHER INFORMATION: Sequence of PCR primer

<400> SEQUENCE: 12
gctgtactag cgacacccac                                                20
```

HAIR CARE PRODUCT

CROSS REFERENCE TO RELATED APPLICATIONS

This application is a divisional of U.S. patent application Ser. No. 11/884,750 filed on Aug. 21, 2007 and entitled HAIR CARE PRODUCT, which in turn is a PCT National Stage of PCT Application No. PCT/JP2006/302560 filed on Feb. 14, 2006, and which claims priority from Japanese Application No. 2005-046151 filed on Feb. 22, 2005, the contents of each being incorporated herein by reference.

TECHNICAL FIELD

The present invention relates to a hair growth tonic, a testosterone 5α-reductase inhibitor, a hair papilla cell growth promoter, a fibroblast growth factor-7 production promoter, a vascular endothelial growth factor production promoter, a bone morphogenetic protein-2 production promoter, and a hair care product.

BACKGROUND ART

Many steroid hormones exhibit their action upon binding to a receptor in the molecular form secreted from the producing organ, but in the case of male hormones called androgens, for example testosterone enters into cells of the target organ and is reduced to 5α-dihydrotestosterone (5α-DHT) by testosterone 5α-reductase, and the 5α-DHT binds to a receptor and exhibits action as an androgen.

Androgens are important hormones, but if androgens act excessively, then various undesirable symptoms are brought about such as male pattern alopecia, hypertrichosis, seborrhea, acne (pimples etc.), benign prostatic hypertrophy, prostatic tumor, and boy's sexual precocity. Methods for inhibiting the effect of excessive androgens, conventionally resorted to with a view of ameliorating the above symptoms include, specifically, methods for inhibiting the generation of active 5α-DHT by inhibiting the action of testosterone 5α-reductase that reduces testosterone to active 5α-DHT. Known herbal medicines having such testosterone 5α-reductase inhibiting action include, for instance, extracts from plants belonging to the *Choerospondias* genus (Patent Document 1), extracts from Majito and/or Kachua (Patent Document 2), extracts from starfruit (Patent Document 3), and extracts from one or two or more plants selected from the group consisting of *Taxus chinensis, Canarium pimela, Heteropanax fragrans* and *Andrographis paniculata* (Patent Document 4).

Hair grows and falls out repeatedly in accordance with a periodical hair cycle (hair growth cycle) that comprises an anagen stage, a catagen stage and a telogen stage. Within this cycle, the stage that extends from the telogen stage to the anagen stage, when new hair follicles are formed, is believed to be the most important stage in hair growth. Herein, hair papilla cells appear to play an important role in the proliferation and differentiation of hair follicle epithelial cells that take place during this stage. Hair papilla cells, which occur on the inner side of hair follicle epithelial cells comprising outer root sheath cells and matrix cells found in the vicinity of hair roots, are cells located at the root stem portion of the hair root, enveloped by a basal membrane. Hair papilla cells play an important role in the proliferation/differentiation of hair follicle epithelial cells and hair formation, for instance by acting on the hair follicle epithelial cells to promote their proliferation (Non-Patent Document 1).

Since hair papilla cells play an important role in the proliferation/differentiation of follicular epithelial cells and hair formation, alopecia may arguably be prevented/ameliorated by promoting the proliferation of hair papilla cells. Known herbal medicines having hair papilla cell growth action include, for instance, extracts from Astragali Radix, extracts from Coptis japonica and extracts from Wedelia chinensis (Patent Documents 5 and 6).

Fibroblast growth factors (FGFs) are multifunctional secreted factors that, in addition to having proliferative activity towards fibroblasts, play important roles, for instance, as morphogenetic factors having cell proliferation/differentiation activity towards various cells, as tissue repair factors that become active during tissue damage, and as metabolism-regulating factors for supporting organism homeostasis. Examples of FGFs include, for instance, FGF-7. In male pattern alopecia, FGF-7 is known to have a low expression level in hair papilla cells (Non-Patent Document 2). Thus, promoting the production of FGF-7 may arguably allow preventing/ameliorating alopecia and the like. Known natural drugs having such FGF-7 production promoting action include, for instance, royal jelly and the like (Patent Document 7).

As is known, the number of capillaries dramatically decreases around the hair root and in hair papilla cells during the telogen stage, when hair growth stops. By contrast, during the anagen stage, when hair is growing, numerous capillaries are formed anew around the hair root and in hair papilla cells. Neoangiogenesis, therefore, appears to be closely linked to, among others, hair growth and development.

As is known, vascular endothelial growth factor (VEGF), discovered in cultures of pituitary gland follicular cells, is a glycoprotein having a molecular weight of 34 to 46 kDa that acts as a specific growth factor for vascular endothelial cells. VEGF is identical to vascular permeability factor (VPF). In addition to pituitary cells, VEGF is produced also by hair papilla cells. The VEGF thus produced has an angiogenic action whereby it acts on vascular endothelial cells, promoting actions of the proliferation and migration of vascular endothelial cells. Thus, promoting the production of VEGF may arguably allow preventing/ameliorating alopecia and the like. Known plant extracts having VEGF production promoting action include, for instance, plants of the *Evolvulus* genus, family Convolvulaceae (Patent Document 8).

Bone morphogenetic protein (BMP) is a protein that forms bone, cartilage, tendon as well as other tissues that are present in bone. This protein, which has a specific inducing activity, exists in bone, and hence it has been suggested that it may be an important regulatory factor in bone repair processes, being also involved in normal maintenance of bone tissues. Numerous such proteins are known, and they are classified into various subfamilies (Non-Patent Document 3). An example of BMP is, for instance, BMP-2. The involvement of BMP-2 in hair follicle formation has been pointed out recently, which has drawn interest into the hair-growth action of BMP-2 (Patent Document 9).

[Patent Document 1] Japanese Unexamined Patent Application Laid-open No. 2003-55162

[Patent Document 2] Japanese Unexamined Patent Application Laid-open No. 2002-241297

[Patent Document 3] Japanese Unexamined Patent Application Laid-open No. 2002-241296

[Patent Document 4] Japanese Unexamined Patent Application Laid-open No. 2002-87976

[Patent Document 5] Japanese Unexamined Patent Application Laid-open No. H09-208431

[Patent Document 6] Japanese Unexamined Patent Application Laid-open No. H11-12134

[Patent Document 7] Japanese Unexamined Patent Application Laid-open No. 2003-192541

[Patent Document 8] Japanese Unexamined Patent Application Laid-open No. 2003-160503

[Patent Document 9] Japanese Unexamined Patent Application Laid-open No. 2005-2068

[Non-Patent Document 1] "Trends Genet", 1992, vol. 8, p. 56-61

[Non-Patent Document 2] "Antiaging Series No. 1 Hair graying, loss and growth in practice" NTS Inc., 2005, p. 91-104

[Non-Patent Document 3] Reddi A. H., "Cytokine Growth Factor Reviews 8", 1997, p. 11-20

DISCLOSURE OF THE INVENTION

Problem to be Solved by the Invention

An object of the invention is to discover a substance having a testosterone 5α-reductase inhibiting action, a hair papilla cell growth promoting action, a fibroblast growth factor-7 (FGF-7) production promoting action, a vascular endothelial growth factor (VEGF) production promoting action or a bone morphogenetic protein-2 (BMP-2) production promoting action, and to provide a hair care product containing this substance therein, as well as a hair growth tonic, a testosterone 5α-reductase inhibitor, a hair papilla cell growth promoter, a fibroblast growth factor-7 (FGF-7) production promoter, a vascular endothelial growth factor (VEGF) production promoter and a bone morphogenetic protein-2 (BMP-2) production promoter each containing this substance as an active ingredient thereof.

Means for Solving the Problem

The hair care product of the present invention contains corosolic acid therein. The hair growth tonic, testosterone 5α-reductase inhibitor, hair papilla cell growth promoter, fibroblast growth factor-7 (FGF-7) production promoter, vascular endothelial growth factor (VEGF) production promoter, or bone morphogenetic protein-2 (BMP-2) production promoter of the present invention contain corosolic acid as an active ingredient thereof.

Advantageous Effect of the Invention

According to the present invention, a hair care product containing corosolic acid therein, and a hair growth tonic, a testosterone 5α-reductase inhibitor, a hair papilla cell growth promoter, a fibroblast growth factor-7 (FGF-7) production promoter, a vascular endothelial growth factor (VEGF) production promoter, and a bone morphogenetic protein-2 (BMP-2) production promoter containing corosolic acid as an active ingredient thereof are provided.

According to the hair care product of the present invention, the testosterone 5α-reductase inhibiting action of corosolic acid allows preventing/ameliorating disorders in which male hormones are involved, while the hair papilla cell growth promoting action of corosolic acid allows preventing/ameliorating alopecia. According to the hair care product of the present invention, the fibroblast growth factor-7 (FGF-7) production promoting action, the vascular endothelial growth factor (VEGF) production promoting action or the bone morphogenetic protein-2 (BMP-2) production promoting action of corosolic acid allow preventing/ameliorating alopecia.

Through the testosterone 5α-reductase inhibiting action of corosolic acid as the effective ingredient, the hair growth tonic of the present invention allows curbing the effect of male hormones and preventing/ameliorating alopecia, while through the hair papilla cell growth promoting action of corosolic acid as the effective ingredient, the hair growth tonic of the present invention allows promoting hair growth/development thereby preventing/ameliorating alopecia. Through the fibroblast growth factor-7 production promoting action, vascular endothelial growth factor production promoting action or bone morphogenetic protein-2 production promoting action of corosolic acid as the effective ingredient, the hair growth tonic of the present invention allows preventing/ameliorating male pattern alopecia. Through the testosterone 5α-reductase inhibiting action of corosolic acid as the effective ingredient, also, the testosterone 5α-reductase inhibitor of the present invention allows curbing the effect of male hormones, and allows preventing/ameliorating disorders in which male hormones are involved. Through the hair papilla cell growth promoting action of corosolic acid as the effective ingredient, moreover, the hair papilla cell growth promoter of the present invention allows promoting the proliferation of hair papilla cells, thereby preventing/ameliorating alopecia. Through the fibroblast growth factor-7 (FGF-7) production promoting action of corosolic acid as the effective ingredient, furthermore, the fibroblast growth factor-7 (FGF-7) production promote of the present invention allows promoting the production of fibroblast growth factor-7, thereby preventing/ameliorating alopecia. Also, the vascular endothelial growth factor (VEGF) production promoter of the present invention allows promoting the production of vascular endothelial growth factor, thereby preventing/ameliorating alopecia. Moreover, the bone morphogenetic protein-2 (BMP-2) production promoter of the present invention allows promoting the production of bone morphogenetic protein-2, thereby preventing/ameliorating alopecia.

BEST MODE FOR CARRYING OUT THE INVENTION

Following is a description of the present invention.

[Hair Growth Tonic, Testosterone 5α-Reductase Inhibitor, Hair Papilla Cell Growth Promoter, Fibroblast Growth Factor-7 Production Promoter, Vascular Endothelial Growth Factor Production Promoter, Bone Morphogenetic Protein-2 Production Promoter]

The hair growth tonic, testosterone 5α-reductase inhibitor, hair papilla cell growth promoter, fibroblast growth factor-7 production promoter, vascular endothelial growth factor production promoter, or bone morphogenetic protein-2 production promoter of the present invention contain corosolic acid as an active ingredient thereof.

Corosolic acid is a kind of triterpenoid compound having a chemical structure represented by the formula below.

[Chemical formula 1]

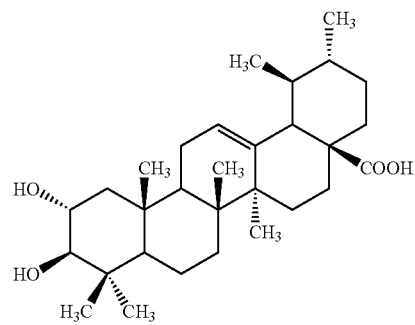

Corosolic acid can be produced by purification and isolation of a plant extract containing corosolic acid, or can be produced by synthesis. When produced synthetically, the synthesis method used is not particularly limited, and hence corosolic acid may be synthesized using a known method (See Japanese Unexamined Patent Application Laid-open No. 2005-29570).

The plant extract containing corosolic acid can be obtained by using an extraction method ordinarily employed for plant extracts. Plants that contain corosolic acid include, for instance, loquat (scientific name: *Eriobotrya japonica*), Banaba (scientific name: *Lagerstroemia speciosa*) and the like.

Loquat (*Eriobotrya japonica*) is an evergreen tree of the Rosaceae family, the fruits of which are edible, and the leaves of which are used, for instance, in therapy of gastroenteric infirmity, neuralgia, diarrhea, and the like. Loquat grows naturally in Japan, Taiwan, China and other areas, where it is easily available. The constituent portion of loquat that can be used as an extraction is not particularly limited, and may include aerial parts such as leaves, branches, bark, trunk, stalk, fruits, seeds, flowers and the like, or roots, or mixtures of these portions, but preferably leaves.

Banaba (*Lagerstroemia speciosa*) is a plant of the Lythraceae family widely distributed over tropical and subtropical areas, such as the Philippines and Australia, where it is easily available. The constituent portion of banaba that can be used as an extraction is not particularly limited, and may include above-ground parts such as leaves, branches, bark, trunk, stalk, fruits, seeds, flowers and the like, or roots, or mixtures of these portions, but preferably leaves.

The plant extract containing corosolic acid can be obtained by drying an extract material, followed by solvent extraction of the dried material as-is or crushed in a primary crusher. Drying may be carried out under sunlight, or employing an ordinarily used dryer. The extract material may be used subjected to a pretreatment, for instance defatting employing an apolar solvent such as hexane or the like. A pretreatment such as defatting allows carrying out the plant extraction using a polar solvent with good efficiency.

Examples of a polar solvent, which is used preferably as the extraction solvent, include, for instance, water, a hydrophilic organic solvent and the like. Preferably, one or a mixture of two or more of such solvents is used in combination at room temperature or at a temperature not exceeding the boiling point of the solvents.

Water that can be used as the extraction solvent includes, for instance, pure water, tap water, well water, mineral spring water, mineral water, hot spring water, spring water, fresh water, as well as any of the foregoing subjected to various treatments. Treatments to which water can be subjected include, for instance, purification, heating, sterilization, filtration, ion exchange, osmotic-pressure adjustment, buffering and the like. Therefore, water that can be used as the extraction solvent in the present invention includes, for instance, purified water, hot water, ion exchange water, saline, phosphate buffer solutions, phosphate buffered saline and the like.

Hydrophilic organic solvents that can be used as the extraction solvent include, for instance, C1 to C5 lower aliphatic alcohols such as methanol, ethanol, propyl alcohol and isopropyl alcohol; lower aliphatic ketones such as acetone and methyl ethyl ketone; and C2 to C5 polyhydric alcohols such as 1,3-butylene glycol, propylene glycol, glycerol and the like.

When a mixed liquid of two or more polar solvents is used as the extraction solvent, the mixing ratio thereof can be suitably adjusted. When using a mixed liquid of water and a lower aliphatic alcohol, for instance, the mixture contains preferably 1 to 90 wt % of lower aliphatic alcohol relative to 10 wt % of water. When using a mixed liquid of water and a lower aliphatic ketone, for instance, the mixture contains preferably 1 to 40 wt % of lower aliphatic ketone relative to 10 wt % of water. When using a mixed liquid of water and a polyhydric alcohol, for instance, the mixture contains preferably 10 to 90 wt % of polyhydric alcohol relative to 10 wt % of water.

The extraction process is not particularly limited, and thus a conventional extraction method can be used, provided that the soluble components contained in the extract material can be eluted by the extraction solvent. For instance, the extract material may be immersed in 5 to 15 times its weight (weight ratio) of extraction solvent, to extract the soluble components, at normal temperature or under reflux heating, followed by removal of the extraction residue by filtration, to yield an extract solution. The solvent is evaporated off the extract to yield a paste-like concentrate, which is the further dried to yield a dry product.

The methods used for purifying and isolating the corosolic acid from the extract solution thus obtained, from the concentrate of the extract solution, or from the dried product of the extract solution are not particularly limited, and ordinary methods may be used. For instance, the plant extract may be subjected to column chromatography using a porous substance such as silica gel or alumina, or using a porous resin such as a styrene divinylbenzene copolymer or polymethacrylate, with sequential elution using water, alcohol, acetone, to yield fractions eluted in alcohol and acetone. The alcohol used for the column chromatography eluate is not particularly limited, and may be, for instance, a C1 to C5 lower aliphatic alcohol such as methanol, ethanol, propyl alcohol, and isopropyl alcohol, or an aqueous solution thereof. The fractions obtained by column chromatography may be purified using any organic compound purification techniques, such as reversed-phase silica gel chromatography using ODS, recrystallization, liquid-liquid countercurrent separation, or column chromatography using an ion exchange resin.

The corosolic acid thus obtained has testosterone 5α-reductase inhibiting action, hair papilla cell growth promoting action, fibroblast growth factor-7 (FGF-7) production promoting action, vascular endothelial growth factor (VEGF) production promoting action, or bone morphogenetic protein-2 (BMP-2) production promoting action, and hence can be used as a hair growth tonic, testosterone 5α-reductase inhibitor, hair papilla cell growth promoter, fibroblast growth factor-7 production promoter, vascular endothelial growth factor production promoter, or bone morphogenetic protein-2 production promoter that exploit such actions. The plant extract obtained by extraction, containing corosolic acid, can be used as-is as the effective ingredient of the hair growth tonic, testosterone 5α-reductase inhibitor, hair papilla cell growth promoter, fibroblast growth factor-7 production promoter, vascular endothelial growth factor production promoter, or bone morphogenetic protein-2 production promoter, but the plant extract is preferably used purified to a higher corosolic acid content. Using a plant extract with increased corosolic acid content allows obtaining a hair growth tonic, testosterone 5α-reductase inhibitor, hair papilla cell growth promoter, fibroblast growth factor-7 production promoter, vascular endothelial growth factor production promoter, or bone morphogenetic protein-2 production promoter that elicit yet more superior usage results. The plant extract containing corosolic acid can comprise an extract solution obtained using a plant containing corosolic acid, a diluted solution or concentrated solution of such extract solution, a dry product obtained by drying such extract solution, or a roughly purified or purified product of the foregoing.

The hair growth tonic, testosterone 5α-reductase inhibitor, hair papilla cell growth promoter, fibroblast growth factor-7 production promoter, vascular endothelial growth factor production promoter, or bone morphogenetic protein-2 production promoter of the present invention may comprise only corosolic acid or a plant extract containing corosolic acid, or may be a pharmaceutical preparation of corosolic acid or of a plant extract containing corosolic acid.

Corosolic acid or a plant extract containing corosolic acid can be made into a pharmaceutical preparation in any drug form, such as powder, granules, liquids or the like, in accordance with ordinary methods, using a pharmacologically acceptable carrier such as dextrin, cyclodextrin or other arbitrary auxiliary agents. Auxiliary agents that can be used include, for instance, excipients, stabilizers, odor-masking agents and the like. The hair growth tonic, testosterone 5α-reductase inhibitor, hair papilla cell growth promoter, fibroblast growth factor-7 production promoter, vascular endothelial growth factor production promoter, or bone morphogenetic protein-2 production promoter, obtained by making corosolic acid or a plant extract containing corosolic acid into a pharmaceutical preparation, may be embodied, for instance, as an ointment, a liquid for external use, an adhesive skin patch or the like.

In the hair growth tonic, testosterone 5α-reductase inhibitor, hair papilla cell growth promoter, fibroblast growth factor-7 production promoter, vascular endothelial growth factor production promoter, or bone morphogenetic protein-2 production promoter of the present invention, a natural extract of the like having a testosterone 5α-reductase inhibiting action, a hair papilla cell growth promoting action, a fibroblast growth factor-7 production promoting action, a vascular endothelial growth factor production promoting action or a bone morphogenetic protein-2 production promoting action can be used, if needed, as an active ingredient blended together with corosolic acid or a plant extract containing corosolic acid.

Through the testosterone 5α-reductase inhibiting action of corosolic acid, the hair growth tonic of the present invention allows curbing the effect of male hormones thereby preventing/ameliorating disorders in which male hormones are involved, while through the hair papilla cell growth promoting action of corosolic acid, the hair growth tonic of the present invention allows promoting hair growth/development thereby preventing/ameliorating alopecia. Through the fibroblast growth factor-7 production promoting action of corosolic acid, furthermore, the hair growth tonic of the present invention allows promoting the production of fibroblast growth factor-7, thereby preventing/ameliorating alopecia. Through the vascular endothelial growth factor production promoting action of corosolic acid, furthermore, the hair growth tonic of the present invention allows promoting the production of vascular endothelial growth factor, thereby preventing/ameliorating alopecia. Through the bone morphogenetic protein-2 production promoting action, moreover, the hair growth tonic of the present invention allows promoting the production of bone morphogenetic protein-2, thereby preventing/ameliorating alopecia. Disorders in which male hormones are involved and which can be prevented/ameliorated by the hair growth tonic of the present invention include, for instance, male pattern alopecia, hypertrichosis, seborrhea, acne (pimples etc.), benign prostatic hypertrophy, prostatic tumor, and boy's sexual precocity. Alopecia that can be prevented/ameliorated by the hair growth tonic of the present invention includes, for instance, male pattern alopecia, alopecia areata, trichotillomania and the like. Other than the above applications, the hair growth tonic of the present invention can be used in all relevant applications for exerting a testosterone 5α-reductase inhibiting action, hair papilla cell growth promoting action, fibroblast growth factor-7 production promoting action, vascular endothelial growth factor production promoting action or bone morphogenetic protein-2 production promoting action.

Through the testosterone 5α-reductase inhibiting action of corosolic acid, also, the testosterone 5α-reductase inhibitor of the present invention allows inhibiting the activity of testosterone 5α-reductase. This allows curbing as a result the effect of male hormones, and allows preventing/ameliorating disorders in which male hormones are involved. Disorders which can be prevented/ameliorated by the testosterone 5α-reductase inhibitor of the present invention include, for instance, male pattern alopecia, hypertrichosis, seborrhea, acne (pimples etc.), benign prostatic hypertrophy, prostatic tumor, and boy's sexual precocity. Other than the above applications, the testosterone 5α-reductase inhibitor of the present invention can be used in all relevant applications for exerting a testosterone 5α-reductase inhibiting action.

Through the hair papilla cell growth promoting action of corosolic acid, the hair papilla cell growth promoter of the present invention allows activating hair papilla cells, and promoting proliferation/differentiation of follicle epithelial cells and hair formation, while preventing transition, during the hair growth cycle, from the anagen stage to the involution and catagen stages, thereby prolonging the anagen stage. As a result, this allows preventing/ameliorating alopecia. Alopecia that can be prevented/ameliorated by the hair papilla cell growth promoter of the present invention includes, for instance, male pattern alopecia, alopecia areata, trichotillomania and the like. Other than the above applications, the hair papilla cell growth promoter of the present invention can be used in all relevant applications for exerting a hair papilla cell growth promoting action.

Through the fibroblast growth factor-7 production promoting action of corosolic acid, the fibroblast growth factor-7 production promoter of the present invention allows promoting the production of fibroblast growth factor-7 in hair papilla cells, thereby preventing/ameliorating alopecia and the like. Other than the above applications, the fibroblast growth factor-7 production promoter of the present invention can be used in all relevant applications for exerting a fibroblast growth factor-7 production promoting action.

Through the vascular endothelial growth factor production promoting action of corosolic acid, the vascular endothelial growth factor production promoter of the present invention allows promoting the production of vascular endothelial growth factor in hair papilla cells, thereby generating new capillaries in the hair papilla cells. These new capillaries allow promoting trichogenesis and hair growth, thereby preventing/ameliorating alopecia and the like. Other than the above applications, the vascular endothelial growth factor production promoter of the present invention can be used in all relevant applications for exerting a vascular endothelial growth factor production promoting action.

Through the bone morphogenetic protein-2 production promoting action of corosolic acid, the bone morphogenetic protein-2 production promoter of the present invention allows promoting the production of bone morphogenetic protein-2, thereby promoting hair growth and development. As a result, this allows preventing/ameliorating alopecia. Other than the above applications, the bone morphogenetic protein-2 production promoter of the present invention can be used in all relevant applications for exerting a bone morphogenetic protein-2 production promoting action.

[Hair Care Product]

The hair care product of the present invention contains corosolic acid therein.

Corosolic acid, which possesses testosterone 5α-reductase inhibiting action, hair papilla cell growth promoting action, fibroblast growth factor-7 production promoting action, vascular endothelial growth factor production promoting action, or bone morphogenetic protein-2 production promoting action, has excellent usability and safety when used on the scalp, and is hence preferable for containing into a hair care product. In the hair care product there may be contained, as-is, corosolic acid or a plant extract containing corosolic acid, or there may be contained a hair growth tonic, testosterone 5α-reductase inhibitor, hair papilla cell growth promoter, fibroblast growth factor-7 production promoter, vascular endothelial growth factor production promoter, or bone morphogenetic protein-2 production promoter obtained by making corosolic acid or a plant extract containing corosolic acid into a pharmaceutical preparation. By blending into a hair care product corosolic acid, or a plant extract containing corosolic acid, or a hair growth tonic, testosterone 5α-reductase inhibitor, hair papilla cell growth promoter, fibroblast growth factor-7 production promoter, vascular endothelial growth factor production promoter, or bone morphogenetic protein-2 production promoter obtained by making corosolic acid or a plant extract containing corosolic acid into a pharmaceutical preparation, the hair care product can be imparted with a testosterone 5α-reductase inhibiting action, hair papilla cell growth promoting action, fibroblast growth factor-7 production promoting action, vascular endothelial growth factor production promoting action, or bone morphogenetic protein-2 production promoting action.

The form of the hair care product of the present invention is not particularly limited, and may be, specifically, a hair tonic, a hair cream, a hair liquid, a shampoo, a conditioner, a pomade or the like.

The blending amount of the active ingredient in the hair care product can be suitably adjusted depending on, for instance, the intended use of the hair care product and the sex and age of the user. Preferable blending ratios, in terms of standard extract, range from 0.0001 to 10 wt %.

Depending on the intended application, the hair care product of the present invention may use, in addition to corosolic acid, arbitrary biologically active substances and/or auxiliary agents. These include, for instance, astringents, bactericides/antimicrobial agents, UV absorbents, moisturizers, cellular activators, anti-inflammatory/anti-allergic agents, antioxidants/active oxygen removers and the like. Using such auxiliary agents affords a synergistic action with other concomitantly-used active ingredients that may bring about more enhanced effects than ordinarily expected.

In the hair care product of the present invention, the testosterone 5α-reductase inhibiting action of corosolic acid allows preventing/ameliorating disorders in which male hormones are involved, while the hair papilla cell growth promoting action of corosolic acid allows preventing/ameliorating alopecia. In the hair care product of the present invention, the fibroblast growth factor-7 production promoting action, the vascular endothelial growth factor production promoting action or the bone morphogenetic protein-2 production promoting action of corosolic acid allow preventing/ameliorating male pattern alopecia. Disorders in which male hormones are involved and which can be prevented/ameliorated by the hair care product of the present invention include, for instance, male pattern alopecia, hypertrichosis, seborrhea, acne (pimples etc.), benign prostatic hypertrophy, prostatic tumor, and boy's sexual precocity. Alopecia that can be prevented/ameliorated by the hair care product of the present invention includes, for instance, male pattern alopecia, alopecia areata, trichotillomania and the like.

The hair growth tonic, testosterone 5α-reductase inhibitor, hair papilla cell growth promoter, fibroblast growth factor-7 production promoter, vascular endothelial growth factor production promoter, bone morphogenetic protein-2 production promoter or hair care product of the present invention are preferably used in humans, but may be also used in animals other than humans, to the extent that the respective effects allow.

EXAMPLES

The present invention is explained in detail below based on producing examples, test examples and blend examples. The scope of the present invention, however, is not limited by these examples.

Producing Example 1

Production of Corosolic Acid 3000 ml of ethanol were added to 300 g of leaves of loquat cut into thin strips, then extraction under reflux was performed at 95° C. for 2 hours, followed by hot filtration. The obtained filtrate was concentrated to dryness in an evaporator, to yield 83 g of loquat leaf extract. The obtained loquat leaf extract was passed through porous adsorption resin (Diaion HP-20, Mitsubishi Chemical Corporation) and was sequentially eluted with 5000 ml of water, 2000 ml of 50 wt % methanol, 2000 ml of methanol, and 2000 ml of acetone. The eluates were chromatographed by thin-layer chromatography (silica gel F60, Merck Ltd.), and after verification of the presence of corosolic acid in the methanol eluate and the acetone eluate, these eluates were combined (27.6 g solids) and were isolated/purified using a silica gel column (mobile phase=chloroform: methanol=20:1 to 30:1, Fuji Silysia Chemical Ltd.), to yield 152 mg of a purified product (sample 1). The results of a $^{13}$C-NMR analysis performed on the purified product are shown below.

<$^{13}$C-NMR Chemical Shift δ (Assigned Carbon)>

17.2(25-C), 17.7(24-C), 17.8(29-C), 17.8(26-C), 19.1(6-C), 21.6(30-C), 24.0(11-C), 24.1(27-C), 25.1(16-C), 28.9(15-C), 29.5(23-C), 31.3(21-C), 33.7(7-C), 37.6(22-C), 38.7(10-C), 38.8(19-C), 39.6(4-C), 40.1(20-C), 40.3(8-C), 42.8(14-C), 48.1(9-C), 48.2(1-C), 48.3(17-C), 53.7(18-C), 56.1(5-C), 68.7(2-C), 84.0(3-C), 125.6(12-C), 139.3(13-C), 179.8(28-C)

The above $^{13}$C-NMR results show that the purified product obtained in Producing example 1 was identified as corosolic acid.

Producing Example 2

Production of 3% Corosolic Acid 1000 ml of 80 wt % ethanol were added to 100 g of leaves of loquat cut into thin strips, then extraction under reflux was performed at 95° C. for 2 hours, followed by hot filtration. The obtained filtrate was concentrated to dryness in an evaporator, to yield 16 g of loquat leaf extract. The obtained loquat leaf extract was analyzed using liquid chromatography under the below-described conditions. The results showed that the extract contained 3 wt % of corosolic acid (sample 2).

<Liquid Chromatography Conditions>
Apparatus: Agilent 1100 (Agilent Technologies)
Stationary phase: Wakosil-II 5C18HG (Wako Pure Chemical Industries, Ltd.)
Column diameter: 4.6 mm
Column length: 250 mm
Mobile phase: 65% acetonitrile
Mobile phase flow rate: 1.2 ml/min.
Detector: UV Producing Example 3

Production of 10% Corosolic Acid 1000 ml of 90 wt % ethanol were added to 100 g of leaves of loquat cut into thin strips, then extraction under reflux was performed at 95° C. for 2 hours, followed by filtration using activated charcoal (Carboraffin, Japan EnviroChemicals, Ltd.). The obtained filtrate was concentrated to dryness in an evaporator, and was suspended in 50 wt % ethanol, then the suspension was filtered with diatomaceous earth. The residue was extracted with 90 wt % ethanol, after which the obtained filtrate was concentrated to dryness in an evaporator, to yield 1.8 g of loquat leaf extract. The obtained loquat leaf extract was analyzed using liquid chromatography under the below-described conditions. The results showed that the extract contained 10 wt % of corosolic acid (sample 3).

<Liquid Chromatography Conditions>
Apparatus: Agilent 1100 (Agilent Technologies)
Stationary phase: Wakosil-II 5C18HG (Wako Pure Chemical Industries, Ltd.)
Column diameter: 4.6 mm
Column length: 250 mm
Mobile phase: 65% acetonitrile
Mobile phase flow rate: 1.2 ml/min.
Detector: UV Test Example 1

Test for Testosterone 5α-Reductase Inhibiting Action

The testosterone 5α-reductase inhibiting action of the corosolic acid obtained in producing examples 1 to 3 (samples 1 to 3) was tested as follows.

4.2 mg of testosterone (Wako Pure Chemical Industries, Ltd.) were dissolved in 1 ml of propylene glycol in a capped V-bottom test tube, then 20 µl of the resulting solution were mixed with 825 µl of a 5 mmol/ml tris-HCl buffer (pH 7.13) containing 1 mg/ml NADPH.

Thereto were then added 80 µl of aqueous-ethanol solutions of each sample and 75 µl of S-9 (rat liver homogenate, Oriental Yeast Co., Ltd.), with mixing and incubation at 37° C. for 30 minutes. The reaction was stopped then through addition of 1 ml of methylene chloride. The samples were centrifuged (1600×g, 10 minutes) to give the methylene chloride layer. The methylene chloride layer was analyzed by gas chromatography under the below-described conditions, for determining the concentrations (µg/ml) of 3α-androstanediol, 5α-dihydrotestosterone (5α-DHT) and testosterone. Controls using the same amount (80 µl) of sample solvent instead of sample solution were treated in the same way, and were also analyzed by gas chromatography.

<Gas Chromatography Conditions>
Apparatus: Shimadzu GC-7 A (Shimadzu Corporation)
Column: DB-1701 (inner diameter: 0.53 mm, length: 30 m, film thickness: 1.0 µm, J&W Scientific Inc.)
Column temperature: 240° C.
Port temperature: 300° C.
Detector: FID
Sample injection amount: 1 µl
Split ratio: 1:2
Carrier gas: nitrogen gas
Carrier gas flow rate: 3 ml/min.

The concentration of 3α-androstanediol, 5α-DHT and testosterone was quantified in accordance with the following method.

Standards of 3α-androstanediol, 5α-DHT and testosterone were dissolved in methylene chloride, the resulting solutions were gas-chromatographed, and then the correspondence between peak areas and compound concentration was determined beforehand based on the composition (µg/ml) of the compounds and their peak areas. The respective concentration per peak area of 3α-androstanediol, 5α-DHT and testosterone after reaction of testosterone with S-9 were calculated based on formula (1) below using the correspondences determined beforehand.

$$A = B \times C/D \quad (1)$$

In the formula, A represents the "concentration of 3α-androstanediol, 5α-DHT or testosterone (µg/ml)", B represents the "peak area of 3α-androstanediol, 5α-DHT or testosterone", C represents the "concentration of the standard (µg/ml)" and D represents the "peak area of the standard".

The conversion rate (concentration ratio of the concentration of 3α-androstanediol and 5α-DHT formed through reduction of testosterone by testosterone 5α-reductase relative to the initial concentration of testosterone) is calculated based on formula (2) below using the compound concentrations calculated based on formula (1).

$$\text{Conversion rate}(\%)(E+F)/(E+F+G) \quad (2)$$

In the formula, E represents the "concentration (µg/ml) of 3α-androstanediol", F represents the "concentration (µg/ml) of 5α-DHT" and G represents the "concentration (µg/ml) of testosterone".

The inhibition rate of testosterone 5α-reductase (%) was calculated based on formula (3) below, using the conversion rate calculated based on formula (2).

$$\text{Inhibition rate}(\%) = (1 - H/I) \times 100 \quad (3)$$

In the formula, H represents "conversion rate upon sample addition" and I represents "conversion rate of control".

The above inhibition rate was measured by decreasing gradually the sample concentration, and the sample concentration $IC_{50}$ (µg/ml), at which the inhibition rate of testosterone 5α-reductase is 50%, was determined by interpolation method.

The test results are shown in Table 1.

TABLE 1

| Sample | $IC_{50}$ (µg/ml) |
| --- | --- |
| Sample 1 | 558 |
| Sample 2 | 556 |
| Sample 3 | 1200 |

As Table 1 shows, corosolic acid proved to have excellent testosterone 5α-reductase inhibiting action.

Test Example 2

Test for Hair Papilla Cell Growth Promoting Action

The hair papilla cell growth promoting action of the corosolic acid obtained in producing examples 1 to 3 (samples 1 to 3) was tested as follows.

Normal human head hair papilla cells were cultured using a papilla cell growth medium (Cell Application Inc.) containing 2% fetal bovine serum (FBS) and proliferation additives, then the cells were retrieved by trypsinization. The retrieved cells were diluted to a cell concentration of $1.0 \times 10^4$ cells/ml using a DMEM medium containing 10% FBS, after which the cells were inoculated in a collagen-coated 96-well plate, at a rate of 200 μl per well, followed by incubation for 3 days. After incubation, the medium was removed and then to the wells there were added 200 μl each of a sample solution in which a respective sample had been dissolved in serum-free DMEM. The wells were then incubated for a further 4 days.

The hair papilla cell growth promoting action was measured using the MTT assay. Once incubation was over, the medium was removed, and then to the wells there was added 100 μl each of MTT dissolved in serum-free DMEM (final concentration 0.4 mg/ml). After 2 hours of incubation, the blue formazan formed inside the cells was extracted with 100 μl of 2-propanol. The absorbance of the extracts was measured at a 570 nm wavelength. Turbidity was measured at the same time, as absorbance at the 650 nm wavelength. The amount of blue formazan formed was taken as the difference between the two absorbances. As a control, the same measurements were carried out for specimens in which serum-less DMEM was added instead of the sample solutions. The hair papilla cell growth promotion rate (%) was calculated from the obtained results using the formula below.

Hair papilla cell growth promotion rate(%)=$A/B \times 100$

In the formula, A represents "absorbance upon sample addition", and B represents "absorbance without sample addition".

The test results are shown in Table 2.

TABLE 2

| Samples | Sample concentration (μg/ml) | Hair papilla cell growth promotion rate (%) |
|---|---|---|
| Sample 1 | 6.25 | 106.1 ± 1.4 |
|  | 1.56 | 111.5 ± 2.2 |
| Sample 2 | 6.25 | 86.2 ± 3.1 |
|  | 1.56 | 105.5 ± 2.5 |
| Sample 3 | 6.25 | 107.7 ± 2.1 |
|  | 1.56 | 108.0 ± 3.0 |

As Table 2 shows, corosolic acid proved to have hair papilla cell growth promoting action.

Test Example 3

FGF-7 Growth Promoting Action Test, VEGF Growth Promoting Action Test and BMP-2 Growth Promoting Action Test The FGF-7 growth promoting action, VEGF growth promoting action and BMP-2 growth promoting action of the corosolic acid obtained in producing examples 1 and 2 (samples 1 and 2) were tested as follows.

Human hair follicle dermal papilla cells (HFDPC) were cultured using a human hair follicle dermal papilla cells growth medium (PCGM), then the cells were retrieved by trypsinization. The retrieved cells were diluted to a cell concentration of $2 \times 10^5$ cells/ml using a DMEM medium containing 10% FBS, after which the cells were inoculated in 60 mm-diameter Petri dishes, at a rate of 5 ml, followed by incubation overnight.

Once incubation was over, the cells were changed to a serum-less DMEM medium to which the samples (sample 1 and 2) had been added after two-hour incubation, then the cells were dissolved in 1 ml of a reagent for RNA extraction (TRIzol, Invitrogen Corporation). After addition of 200 μl of chloroform to the solutions, these were centrifuged (12000 rpm, 4° C., 15 minutes) and the top RNA layer was isolated. The RNA layer was concentrated in isopropanol. The total RNA concentrated and precipitated was dissolved in a TE solution (10 mM Tris-HCl/1 mM EDTA, pH 8.0), and was taken as a total RNA standard (sequence numbers 1 to 3) used in a template of quantitative RT-PCR for measuring the mRNA expression level of the FGF-7 gene, the VEGF gene and the BMP-2 gene. As a control, total RNA was prepared as described above for cells to which no sample was added.

After synthesizing single-strand DNA from 500 ng of total RNA in a PCR apparatus (TaKaRa PCR Thermal Cycler MP, TAKARA BIO INC.), the FGF-7 gene (sequence no. 4), the VEGF gene (sequence no. 5), the BMP-2 gene (sequence no. 6), and the G3PDH gene as an internal standard were amplified by PCR reaction, from the single-strand DNA, using specific sense primers (sequence nos. 7 to 9) and antisense primers (sequence nos. 10 to 12) of the respective genes, then 10 μl of the amplified product were electrophoresed on 1.2% agarose gel. After electrophoresis, the gels were stained with ethidium bromide and were imaged under a transilluminator using a DC120 Zoom Digital camera (KODAK). Then the RT-PCR products were quantitatively measured using KODAK 1D Image Analysis Software EDAS290 Version3.5. The PCR reaction liquid was prepared in accordance with the supporting material of the reagent (TaKaRa RNA PCR Kit (AMV) Ver3.0).

The band intensities of the FGF-7 gene, the VEGF gene and the BMP-2 gene as amplified by RT-PCR were corrected through division by the band intensity of the G3PDH gene, on the basis of total RNA standards prepared from a culture to which no samples were added, and cultures to which respective samples were added. The mRNA expression promotion rate of the FGF-7 gene, the VEGF gene and the BMP-2 gene were obtained based on the following formula.

mRNA expression promotion rate(%)=$(A/B) \times 100$

In the formula A represents "corrected value upon sample addition" and B represents "corrected value without sample addition (control)".

The results are shown in Table 3.

TABLE 3

| Sample | Sample concentration (μg/ml) | mRNA expression promotion rate (%) FGF-7 mRNA | VEGF mRNA | BMP-2 mRNA |
|---|---|---|---|---|
| Sample 1 | 0.25 | 124.8 ± 7.2 | 106.7 ± 4.5 | 135.3 ± 5.5 |
|  | 0.06 | 122.9 ± 8.5 | 121.8 ± 3.5 | 105.3 ± 3.8 |
| Sample 2 | 10 | 116.1 ± 1.3 | 112.4 ± 4.2 | 146.5 ± 9.7 |
|  | 2.5 | 127.4 ± 6.0 | 135.0 ± 4.2 | 101.5 ± 1.6 |

Table 3 shows that corosolic acid proved to promote the mRNA expression of the FGF-7 gene, the VEGF gene and the BMP-2 gene. This indicates that corosolic acid has fibroblast growth factor-7 production promoting action, vascular endothelial growth factor production promoting action or bone morphogenetic protein-2 production promoting action.

Blend Example 1

A hair tonic having the following composition was produced using an ordinary method.

| | |
|---|---|
| Corosolic acid (Producing Example 1) | 0.1 g |
| Pyridoxine hydrochloride | 0.1 g |
| Resorcin | 0.01 g |
| D-pantothenyl alcohol | 0.1 g |
| Dipotassium glycyrrhizinate | 0.1 g |
| *Swertia* extract | 0.2 g |
| L-menthol | 0.05 g |
| 1,3-butylene glycol | 4.0 g |
| Carrot extract | 0.5 g |
| *Sophorae radix* extract | 0.3 g |
| Chamomile extract | 0.2 g |
| Salicylic acid | 0.2 g |
| Sodium pyrrolidone carboxylate | 1.0 g |
| Ethanol | 25.0 g |
| Fragrance | Suitable amount |
| Purified water | Remainder |
| | (taking total amount to be 100 g) |

Blend Example 2

A hair lotion having the following composition was produced using an ordinary method.

| | |
|---|---|
| Corosolic acid (Producing Example 1) | 0.01 g |
| 1,3-butylene glycol | 6.0 g |
| Ethanol | 8.0 g |
| Polyoxyethylene hydrogenated castor oil (40 E.O.) | 1.0 g |
| Polyoxysorbitan monostearate (20 E.O.) | 1.5 g |
| Stearyl glycyrrhetinate | 0.2 g |
| Enmeiso extract | 0.5 g |
| Oil-soluble licorice extract | 0.02 g |
| Hinokitiol | 0.05 g |
| Urea | 3.0 g |
| Niacin | 0.1 g |
| Diphenhydramine hydrochloride | 0.1 g |
| Tocopherol acetate | 0.05 g |
| Methyl paraoxybenzoate | 0.1 g |
| Phenoxyethanol | 0.3 g |
| L-menthol | 0.2 g |
| Purified water | Remainder |
| | (taking total amount to be 100 g) |

Blend Example 3

A hair growth tonic having the following composition was produced using an ordinary method.

| | |
|---|---|
| Corosolic acid (Producing Example 1) | 0.5 g |
| Hinokitiol | 0.1 g |
| Glycyrrhetic acid | 0.1 g |
| Cepharanthin | 0.02 g |
| Polyoxyethylene hydrogenated castor oil (20 E.O.) | 1.5 g |
| 1,3-butylene glycol | 3.0 g |
| Ethanol | 60.0 g |
| Tocopherol acetate | 0.1 g |
| Carrot extract | 0.1 g |
| Capsicum tincture | 2.0 g |
| Garlic extract | 0.5 g |
| Photosensitizing dye 301 | 0.005 g |
| Pyridoxine hydrochloride | 0.05 g |
| D,L-menthol | 0.3 g |
| Purified water | Remainder |
| | (taking total amount to be 100 g) |

Blend Example 4

A shampoo having the following composition was produced using an ordinary method.

| | |
|---|---|
| Corosoilic acid (Producing Example 1) | 1.0 g |
| Polyoxyethylene triethanolamine lauryl sulfate | 14.0 g |
| Ethylene glycol distearate | 2.0 g |
| Lauryl dimethylaminoacetate betaine | 4.0 g |
| Lauric diethanolamide | 5.0 g |
| Glycerol | 2.0 g |
| Keratin hydrolysate | 3.0 g |
| Soapberry extract | 0.2 g |
| Soapbark extract | 1.0 g |
| *Engelhardia roxburghiana* extract | 0.5 g |
| Cork tree bark extract | 0.3 g |
| Rosemary extract | 0.5 g |
| *Aloe* extract | 0.2 g |
| Peach leaf extract | 0.3 g |
| Seaweed (brown algae) extract | 0.5 g |
| Horse chestnut extract | 0.3 g |
| Methyl paraoxybenzoate | 0.1 g |
| Fragrance | 0.05 g |
| Purified water | Remainder |
| | (taking total amount to be 100 g) |

INDUSTRIAL APPLICABILITY

A hair growth tonic, a testosterone 5α-reductase inhibitor, a hair papilla cell growth promoter, a fibroblast growth factor-7 production promoter, a vascular endothelial growth factor production promoter, a bone morphogenetic protein-2 production promoter or a hair care product of the present invention greatly contributes to preventing/ameliorating disorders, alopecia and so on in which male hormones are involved.

The invention claimed is:

1. A method for promoting hair growth in a human in need of promoting hair growth, comprising steps of:
   preparing a hair growth tonic containing corosolic acid as an active ingredient thereof, and
   administering an effective amount of the hair growth tonic to the human body for promoting hair growth.

2. A method for inhibiting an activity of testosterone 5α-reductase in a human in need of inhibiting the activity of the 5α-testosterone reductase, comprising steps of:
   preparing a testosterone 5α-reductase inhibitor containing corosolic acid as an active ingredient thereof, and
   administering an effective amount of the testosterone 5α-reductase inhibitor to the human body for inhibiting the activity of the 5α-testosterone reductase.

3. A method for promoting a growth of hair papilla cell in a human in need of promoting the growth of hair papilla cell, comprising steps of:
   preparing a hair papilla cell growth promoter containing corosolic acid as an active ingredient thereof, and
   administering an effective amount of the hair papilla cell growth promoter to the human body for promoting the growth of hair papilla cell.

4. A method for promoting production of fibroblast growth factor-7 in a human in need of promoting production of fibroblast growth factor-7, comprising steps of:
   preparing a fibroblast growth factor-7 production promoter containing corosolic acid as an active ingredient thereof, and
   administering an effective amount of the fibroblast growth factor-7 production promoter to the human body for promoting production of fibroblast growth factor-7.

5. A method for promoting production of vascular endothelial growth factor in a human in need of promoting production of vascular endothelial growth factor, comprising steps of:
   preparing a vascular endothelial growth factor production promoter containing corosolic acid as an active ingredient, and
   administering an effective amount of the vascular endothelial growth factor production promoter to the human body for promoting production of vascular endothelial growth factor.

6. A method for promoting production of bone morphogenetic protein-2 in a human or an animal in need of promoting hair growth and development, comprising steps of:
   preparing a bone morphogenetic protein-2 production promoter containing corosolic acid as an active ingredient, and
   administering an effective amount of the bone morphogenetic protein-2 production promoter to the human or the animal body for promoting hair growth and development.

7. A method for treating a disorder selected from the group consisting of alopecia, hypertrichosis, seborrhea, benign prostatic hypertrophy, prostatic tumor and boy's sexual precocity, in a patient in need thereof, comprising steps of:
   preparing a corosolic acid, and
   administering an effective amount of the corosolic acid to the patient for alleviating the disorder selected from the group consisting of alopecia, hypertrichosis, seborrhea, benign prostatic hypertrophy, prostatic tumor and boy's sexual precocity.

* * * * *